US006366871B1

(12) United States Patent
Geva

(10) Patent No.: US 6,366,871 B1
(45) Date of Patent: Apr. 2, 2002

(54) PERSONAL AMBULATORY CELLULAR HEALTH MONITOR FOR MOBILE PATIENT

(75) Inventor: Yakov Geva, Rishon Le Zion (IL)

(73) Assignee: Card Guard Scientific Survival Ltd., Rechovot (IL)

(*) Notice: Subject to any disclaimer, the term of this patent is extended or adjusted under 35 U.S.C. 154(b) by 0 days.

(21) Appl. No.: 09/261,136

(22) Filed: Mar. 3, 1999

(51) Int. Cl.⁷ .............................................. H04Q 7/22
(52) U.S. Cl. ................... 702/188; 340/825.56
(58) Field of Search ................. 702/188, 127, 702/62, 122; 340/825.57, 825.58, 825.56

(56) References Cited

U.S. PATENT DOCUMENTS

| 5,652,570 A | | 7/1997 | Lepkofker |
| 5,701,894 A | * | 12/1997 | Cherry et al. ............... 128/630 |
| 5,724,025 A | * | 3/1998 | Tavori ......................... 340/573 |
| 5,877,675 A | * | 3/1999 | Rebstock et al. ...... 340/286.07 |
| 5,929,761 A | * | 7/1999 | Van der Laan et al. .. 340/573.1 |
| 6,083,248 A | * | 4/2000 | Thompson ................... 607/30 |
| 6,072,396 A | * | 6/2000 | Gaukel ..................... 340/573.4 |
| 6,084,510 A | * | 7/2000 | Lemelson et al. .......... 340/539 |

* cited by examiner

Primary Examiner—Marc S. Hoff
Assistant Examiner—Edward Raymond
(74) Attorney, Agent, or Firm—Eitan, Pearl, Latzer & Cohen-Zedek

(57) ABSTRACT

Ambulatory patient monitoring apparatus including a portable housing including at least one physiological data input device operative to gather physiological data of the patient, location determination circuitry operative to determine geographic location information of the patient, cellular telephone communications circuitry for communicating the physiological data and the geographic location information to a central health monitoring station, voice communications circuitry whereby the patient conducts voice communications with a clinician at the central health monitoring station, digital signal processing circuitry for processing signals associated with any of the physiological data input device, the location determination circuitry, the cellular telephone communications circuitry, and the voice communications circuitry, and control circuitry for controlling any of the digital signal processing circuitry, the physiological data input device, the location determination circuitry, the cellular telephone communications circuitry, and the voice communications circuitry.

26 Claims, 12 Drawing Sheets

PERSONAL AMBULATORY CELLULAR HEALTH MONITOR FOR MOBILE PATIENT

FIELD OF THE INVENTION

The present invention relates to patient monitoring systems in general, an in particular to apparatus and methods for monitoring a mobile patient's physiological condition and wireless reporting of same.

BACKGROUND OF THE INVENTION

Continuously monitoring a patient's physiological condition generally requires the patient's hospitalization, usually at great cost, especially where long term monitoring is required. In some circumstances a wide variety of out-patient monitoring devices may be used to monitor the physiology of patients who are physically outside of the hospital. Some out-patient monitoring devices have a limited range of operation, requiring monitored patients to remain close to a receiving station and thus limiting his mobility. Other devices are adapted for monitoring mobile or ambulatory patients while they move about in a vehicle or on foot and have a wide range of operation.

One such group of devices includes holter devices which generally record a patient's physiological data, such as the patient's ECG, during predetermined period of time for examination at later time. Other devices include event recorders. These devices provide for the captured of a patient's physiological data during a physiological "event," such as a cardiac arrhythmia or an episode of patient discomfort. These devices may be patient activated or activated automatically when physiological data are detected which meet predefined event criteria.

Holter devices and event recorders typically require that a patient return to the hospital periodically in order to transfer the recorded data. Some of these devices provide for transmission via telephone or other communications facilities to a remote location for interpretation by a clinician. These devices generally require additional communication and medical testing devices to be present at patient location. In the case of event recorders, unnecessary delay between event recording and transmission is often introduced where such additional devices are not present during the event.

The mobility of high-risk patients must be weighed against the need to monitor a patient's location in order to provide a patient with emergency medical attention should a dangerous event occur.

SUMMARY OF THE INVENTION

The present invention seeks to provide improved apparatus and methods for monitoring a mobile patient's physiological condition and reporting the patient's physiological data as well as the patient's location which overcome the disadvantages of the prior art.

It is an object of the present invention to provide an improved ambulatory monitoring device which monitors a patient's physiological condition and location, contacts a central station, transmits the patient's physiological data and the patient's location coordinates to the central station, and provides voice communications between the patient and a clinician at the central station. The monitoring may be initiated by the patient with or without a periodic reminder, may be initiated by the device itself, may be initiated by the clinician through instruction to the patient, and/or may be performed continuously. The communication between the monitoring device and the central station may be initiated by the patient, by the device itself, or by the clinician at the central station.

There is thus provided in accordance with a preferred embodiment of the present invention ambulatory patient monitoring apparatus including a portable housing including at least one physiological data input device operative to gather physiological data of the patient, location determination circuitry operative to determine geographic location information of the patient, cellular telephone communications circuitry for communicating the physiological data and the geographic location information to a central health monitoring station, voice communications circuitry whereby the patient conducts voice communications with a clinician at the central health monitoring station, digital signal processing circuitry for processing signals associated with any of the physiological data input device, the location determination circuitry, the cellular telephone communications circuitry, and the voice communications circuitry, and control circuitry for controlling any of the digital signal processing circuitry, the physiological data input device, the location determination circuitry, the cellular telephone communications circuitry, and the voice communications circuitry.

Further in accordance with a preferred embodiment of the present invention the at least one physiological data input device is assembled within the housing.

Still further in accordance with a preferred embodiment of the present invention the at least one physiological data input device is at least partially external to the housing.

Additionally in accordance with a preferred embodiment of the present invention the external portion of the at least one physiological data input device is connected to the via housing via a connector.

Moreover in accordance with a preferred embodiment of the invention the location determination circuitry includes GPS circuitry.

Further in accordance with a preferred embodiment of the present invention the control circuitry operates the physiological data input device continuously.

Still further in accordance with a preferred embodiment of the present invention the control circuitry operates the physiological data input device upon initiation by the patient.

Additionally in accordance with a preferred embodiment of the present invention the control circuitry includes a memory for storing any of the physiological data.

Moreover in accordance with a preferred embodiment of the present invention the control circuitry is operative to simultaneously store a first portion of the physiological data in the memory in FIFO fashion and a second portion of the physiological data in the memory that is write-protected with respect to the first portion.

Further in accordance with a preferred embodiment of the present invention the memory includes preset parameters adapted for comparison with the physiological data.

Still further in accordance with a preferred embodiment of the present invention the control circuitry is operative to determine whether the physiological data are within the preset parameters.

Additionally in accordance with a preferred embodiment of the present invention the control circuitry is operative to initiate contact with the central health monitoring station when the physiological data are determined to be outside of the preset parameters.

Moreover in accordance with a preferred embodiment of the present invention the memory includes preprogrammed instructions for output to the patient via either of a display and a speaker.

There is also provided in accordance with a preferred embodiment of the present invention a system for monitoring a patient, the system including a central health monitoring station, and a portable housing for use by the patient, the portable housing including at least one physiological data input device operative to gather physiological data of the patient, location determination circuitry operative to determine geographic location information of the patient, cellular telephone communications circuitry for communicating the physiological data and the geographic location information to the central health monitoring station, voice communications circuitry whereby the patient conducts voice communications with a clinician at the central health monitoring station, digital signal processing circuitry for processing signals associated with any of the physiological data input device, the location determination circuitry, the cellular telephone communications circuitry, and the voice communications circuitry, and control circuitry for controlling any of the digital signal processing circuitry, the physiological data input device, the location determination circuitry, the cellular telephone communications circuitry, and the voice communications circuitry.

There is additionally provided in accordance with a preferred embodiment of the present invention a method for monitoring a patient, the method including providing a portable housing for use by the patient, the portable housing including at least one physiological data input device operative to gather physiological data of the patient, location determination circuitry operative to determine geographic location information of the patient, cellular telephone communications circuitry for communicating the physiological data and the geographic location information to the central health monitoring station, voice communications circuitry whereby the patient conducts voice communications with a clinician at the central health monitoring station, digital signal processing circuitry for processing signals associated with any of the physiological data input device, the location determination circuitry, the cellular telephone communications circuitry, and the voice communications circuitry, and control circuitry for controlling any of the digital signal processing circuitry, the physiological data input device, the location determination circuitry, the cellular telephone communications circuitry, and the voice communications circuitry, gathering physiological data of the patient, determining the geographic location of the patient, and communicating the physiological data and the geographic location to the central health monitoring station.

Further in accordance with a preferred embodiment of the present invention the method further includes analyzing the physiological data, and providing a response based on the physiological data.

Still further in accordance with a preferred embodiment of the present invention the gathering step is performed in response to activation by the patient.

Additionally in accordance with a preferred embodiment of the present invention the method further includes activating an alarm prior to the activation by the patient.

Moreover in accordance with a preferred embodiment of the present invention the gathering step is performed independently from activation by the patient.

Further in accordance with a preferred embodiment of the present invention the gathering step includes storing the physiological data in a memory.

Still further in accordance with a preferred embodiment of the present invention the communicating step is performed in response to activation by the patient.

Additionally in accordance with a preferred embodiment of the present invention the communicating step is performed independently from activation by the patient upon the memory becoming full.

Moreover in accordance with a preferred embodiment of the present invention the method further includes clearing a portion of the memory corresponding to the physiological data that has been communicated to the control health monitoring station.

Further in accordance with a preferred embodiment of the present invention the storing step includes simultaneously storing a first portion of the physiological data in the memory in FIFO fashion and a second portion of the physiological data in the memory that is write-protected with respect to the first portion.

Still further in accordance with a preferred embodiment of the present invention the communicating step includes establishing a communications link with the central health monitoring station in response to activation by the patient.

Additionally in accordance with a preferred embodiment of the present invention the communicating step includes establishing a communications link with the central health monitoring station in response to an incoming communication from the central health monitoring station.

Moreover in accordance with a preferred embodiment of the present invention the communicating step includes determining whether the physiological data are outside of preset parameters, and establishing a communications link with the central health monitoring station when the physiological data are determined to be outside of the preset parameters.

Further in accordance with a preferred embodiment of the present invention the providing a response step includes voice-communicating an instruction to the patient.

Still further in accordance with a preferred embodiment of the present invention the providing a response step includes providing the patient's location to medical emergency personnel and dispatching the personnel to the patient's location.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
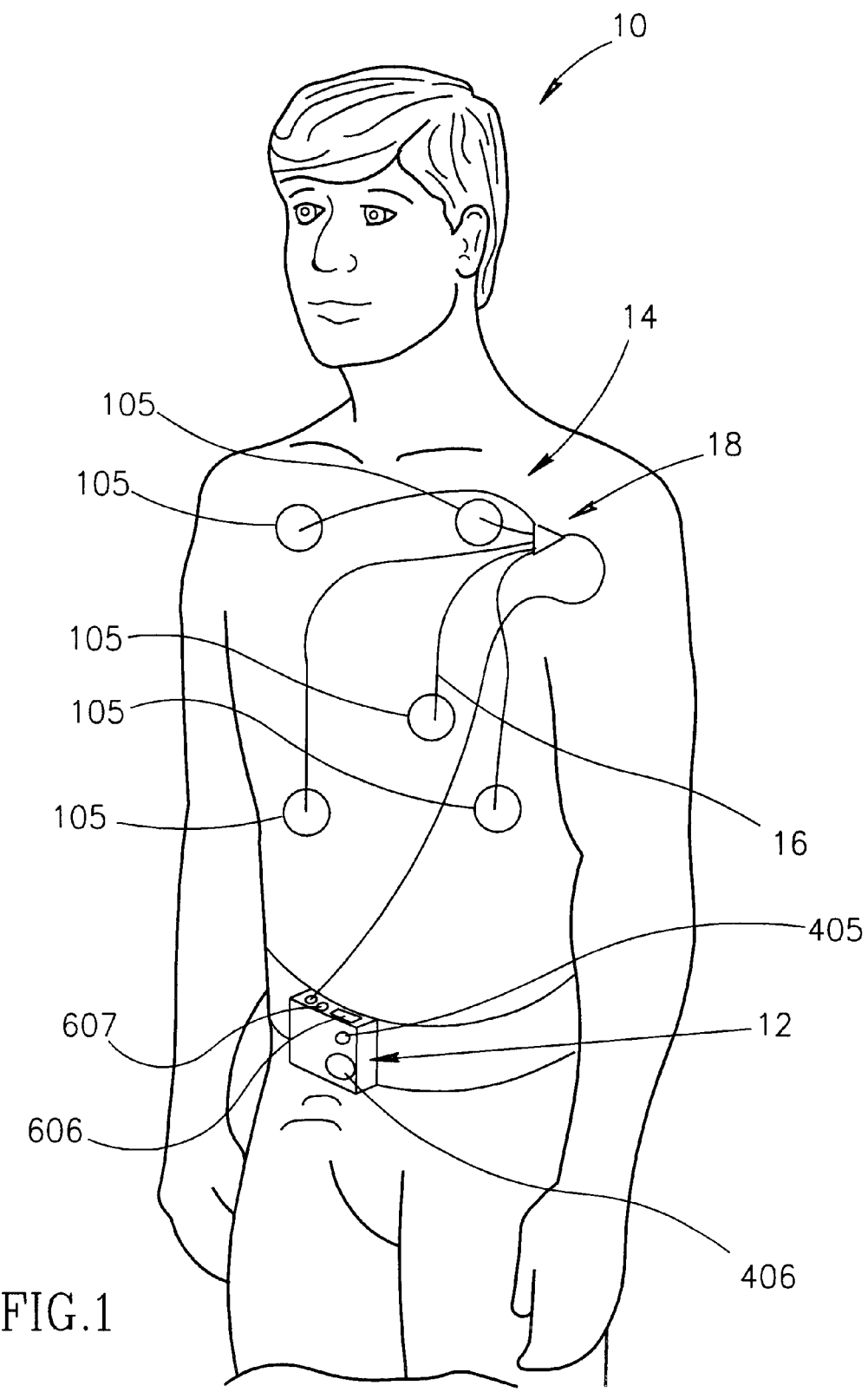
FIG. 1 is a simplified pictorial illustration of a personal ambulatory cellular health monitor, constructed and operative in accordance with a preferred embodiment of the present invention.

Reference is now made to FIG. 1 which is a simplified pictorial illustration of a personal ambulatory cellular health monitor, constructed and operative in accordance with a preferred embodiment of the present invention. A patient 10 is shown wearing a personal ambulatory cellular health monitor 12 which preferably monitors the physiological condition of patient 10, records physiological data, and transmits some or all of the data, as well as patient 10's location, via a cellular telephone network to a central medical monitoring station (not shown). Monitor 12 preferably includes a microphone 405, a speaker 416, a display 606 and a keypad 607. Monitor 12 is preferably adapted to be connected to one or more physiological data input devices such as an electrocardiograph (ECG) input device, generally designated 14, having one or more ECG electrodes 105 each connected by a wire 16 to a terminus 18 which is connected to monitor 12. Other physiological data input devices known in the art may likewise be connected to monitor 12 or otherwise built into monitor 12, as is described in greater detail hereinbelow with reference to FIG. 2, including devices for monitoring blood oxygen saturation, respiration, blood glucose, blood pressure, lung function, $SpO_2$ saturation, and temperature.

Figure 2A:
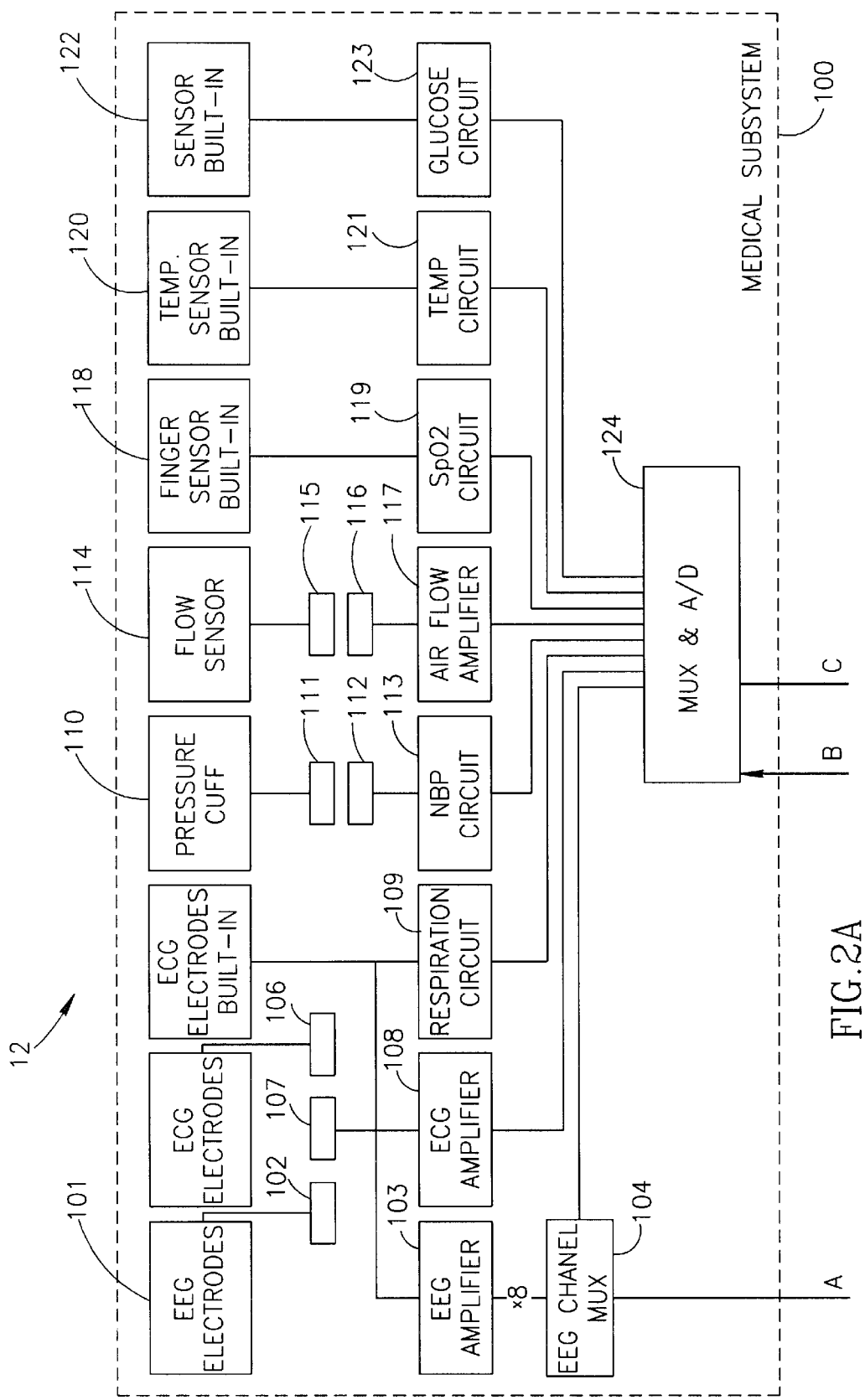
FIG. 2 is a simplified block diagram illustration of the personal ambulatory cellular health monitor of FIG. 1, constructed and operative in accordance with a preferred embodiment of the present invention.
Figure 2B:
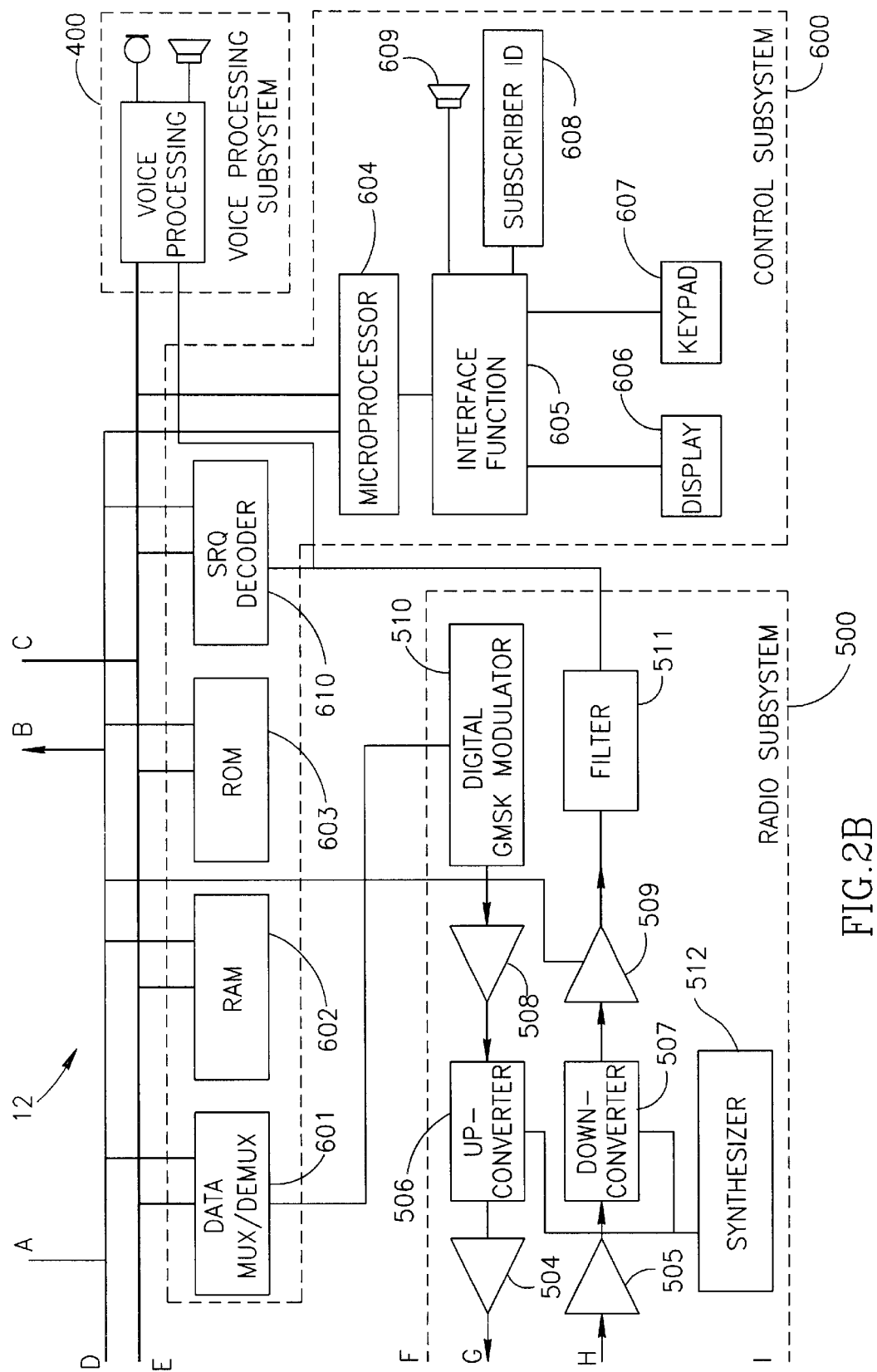
Figure 2C:
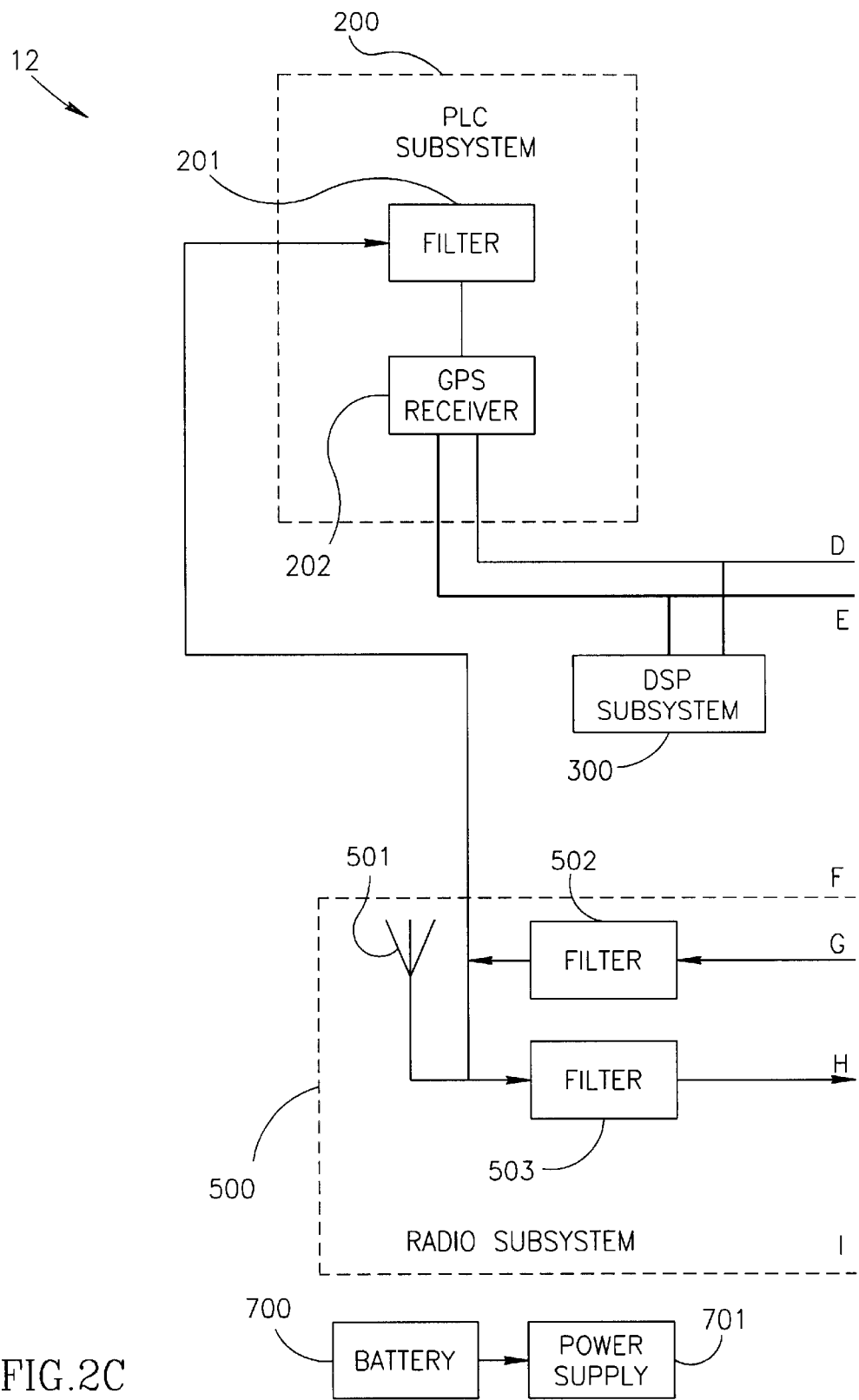

Additional reference is now made to FIG. 2 which is simplified block diagram illustration of the personal ambulatory cellular health monitor 12 of FIG. 1, constructed and operative in accordance with a preferred embodiment of the present invention. Monitor 12 typically includes a medical subsystem 100, a personal location subsystem (PLC) 200, a digital signal processing (DSP) subsystem 300, a voice processing subsystem 400, a radio subsystem 500 and a control subsystem 600.

Medical subsystem 100 typically includes one or more built-in and/or external physiological sensors and associated electronic signal conditioning circuits and a set of sensors. Built-in sensors may include a finger optical sensor 118 for $SpO_2$, an optical sensor 122 for measuring blood glucose, a, temperature sensor 120, and ECG electrodes 105A.

External sensors for plug-in connection to monitor 12 may include EEG electrodes 101, ECG electrodes 105, a pressure cuff 110 for measuring NIBP, and an air flow sensor 114 for measuring spirometry. EEG electrodes 101 and ECG electrodes 105 are equipped with connector plugs 102 and 106 respectively which may be identical for connection to monitor 12 via a single receptacle connector 107. Connector 107 may include an electronic circuit which automatically recognizes which of EEG electrodes 101 and ECG electrodes 105 is plugged in a receptacle 107. Pressure cuff 110 also typically includes a plug 111 designed to be connected to a receptacle 112, as does flow sensor 114 typically include a plug 115 designed to be connected to a receptacle 116.

An EEG amplifier circuit 103 connected to EEG electrodes 101, typically eight EEG electrodes, capture EEG signals, amplifies and normalizes the signal, and provides the normalized signal to an EEG channel multiplexer (MUX) 104 which in turn provides the normalized signals to a multiplexer and analog to digital converter circuit (MUX & A/D) 124.

An ECG amplifier circuitry 108 connected to ECG electrodes 105, typically two or more ECG electrodes, captures ECG signals, amplifies and normalizes the signal, and provides the normalized signal to MUX & A/D 124.

ECG electrodes 105 are also preferably connected to a respiration circuit 109 which measures the AC voltage drop between ECG electrodes 105, amplifies the voltage drop, and normalizes the signal. Circuit 109 then provides the normalized signal to MUX & A/D 124.

An NIBP circuit 113 connected to pressure cuff 110 captures a blood pressure signal, amplifies and normalizes the signal, and provides the normalized signal to MUX & A/D 124.

An air flow amplifier 117 connected to air flow sensor 114 captures an air flow signal, amplifies and normalizes the signal, and provides the normalized signal to MUX & A/D 124.

An $SpO_2$ circuit 119 connected to finger sensor 118 captures an oxygen saturation signal, amplifies and normalizes the signal, and provides the normalized signal to MUX & A/D 124.

A temperature circuit 121 connected to temperature sensor 120 captures a temperature signal, amplifies and normalizes the signal, and provides the normalized signal to MUX & A/D 124.

A glucose circuit 123 connected to optical sensor 122 captures a blood glucose signal, amplifies and normalizes the signal, and provides the normalized signal to MUX & A/D 124.

Signals received at MUX & A/D 124 are digitized and provided to DSP subsystem 300 where they are processed using known techniques and stored in a RAM memory 602.

The personal location subsystem (PLC) 200 determined the location of patient 10. PLC subsystem 200 preferably includes known location determination circuitry such as GPS components including a GPS receiver 202 and a filter 201 which is tuned to a known GPS frequency for CPS satellite communication via a built-in antenna 501 typically shared by radio subsystem 500. PLC subsystem 200 preferably receives the pseudo range (PR) and pseudo range dot (PRD) from GPS satellites in communication range. The GPS receiver preferably operates in aided mode enabling "snapshot" operation as is known in GPS systems. Patient 10's position and velocity data is preferably transmitted via radio subsystem 500 to a central medical monitoring station together with measured physiological data as is described in greater detail hereinbelow. PLC 200 preferably determines the patient's location once monitor 12 is in contact with the central medical monitoring station, such as when contact is established by the patient, a clinician at the central medical monitoring station, or automatically by monitor 12 during a patient event or otherwise as is described in greater detail hereinbelow with reference to FIGS. 5–7B. The location information determined by GPS receiver 202 may be stored in memory 602 or may be transmitted immediately once the patient's location is determined.

Data stored in RAM memory 602 may be transmitted immediately upon receipt at memory 202 or at a later time via radio subsystem 500 to a central medical monitoring station for analysis by a physician or clinician. Radio subsystem 500 typically includes cellular telephone communications circuitry including a filter 502, a power amplifier 504, a frequency up-converter 506, an amplifier 508, and a GMSK modulator 510 which generates, modulates, and amplifies a signal for transmission via antenna 501. Radio subsystem 500 also typically includes a filter 503 and an amplifier 505 which filters and amplifies incoming signals received via antenna 501. The signal is then processed at a frequency down-converter 507, an intermediate reception amplifier 509, and a filter 511, whereupon the processed incoming signal is provided to voice processing subsystem 400 for output. A synthesizer 512 is also provided which, in conjunction with frequency up-converter 506 and frequency down-converter 507, performs the frequency conversions required for signal transmission and reception.

Control subsystem 600 typically includes control circuitry including a data MUX/DEMUX 601 which provides simultaneous multiple analog data channel conversion to digital data and vice versa, RAM memory 602, a ROM memory 603, a microprocessor 604, interface function circuitry 605 via which microprocessor 604 communicates with the various subsystems, display 606, keypad 607, a subscriber ID 608 for cellular telephone identification such as is known with GSM systems, an alarm 609, and a service request decoder (SRQ) 610 which decodes incoming signals to determine if the signal is a voice communication or a control signal and, if the latter, informs microprocessor 604 of the incoming control signal and the nature of the control instructions, such as data download, data upload, etc. Microprocessor 604 preferably controls the operation of monitor 12, including medical subsystem 100, PLC subsystem 200, DSP subsystem 300, voice processing subsystem 400, and radio subsystem 500. Control subsystem 600 also manages common resources such as DSP subsystem 300, Data MUX/DEMUX 601, RAM memory 602, and ROM memory 603 among the various subsystems, and controls data flow between subsystems.

Monitor 12 is typically powered by a battery 700 and a power supply 701.

Figure 3:
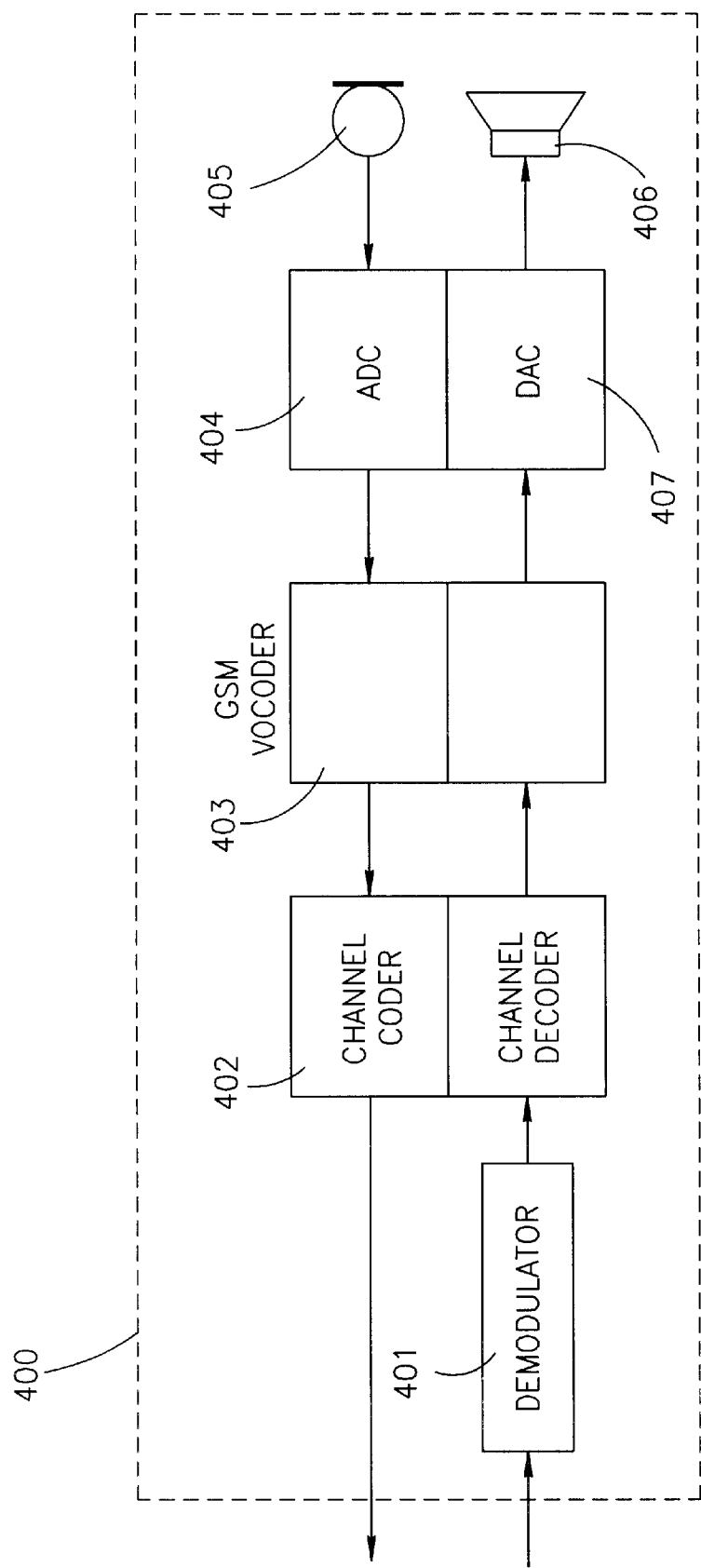
FIG. 3 is a simplified block diagram illustration of voice processing subsystem 400 of FIG. 2, constructed and operative in accordance with a preferred embodiment of the present invention.

Additional reference is now made to FIG. 3 which is a simplified block diagram illustration of voice processing subsystem 400 or FIG. 2, constructed and operative in accordance with a preferred embodiment of the present invention. Voice processing subsystem 400 typically voice communications circuitry including a demodulator 401, a channel coder/decoder 402, a GSM voice coder (vocoder) 403, microphone 405, speaker 406, an analog-to-digital converter (ADC) 404, and a digital-to-analog converter (DAC) 407. Signal received by radio subsystem 400 are demodulated at demodulator 401, decoded at channel coder/decoder 402, processed at voice coder 403, converted to analog signals at DAC 407, and output via speaker 406. Voice signals input via microphone 405 are digitized at ADC 404, processed at voice coder 403, channel encoded at channel coder/decoder 402, and provided to data MUX/DEMUX 601 aid finally to digital GMSK modulator 510 for transmission via radio subsystem 500.

Figure 4:
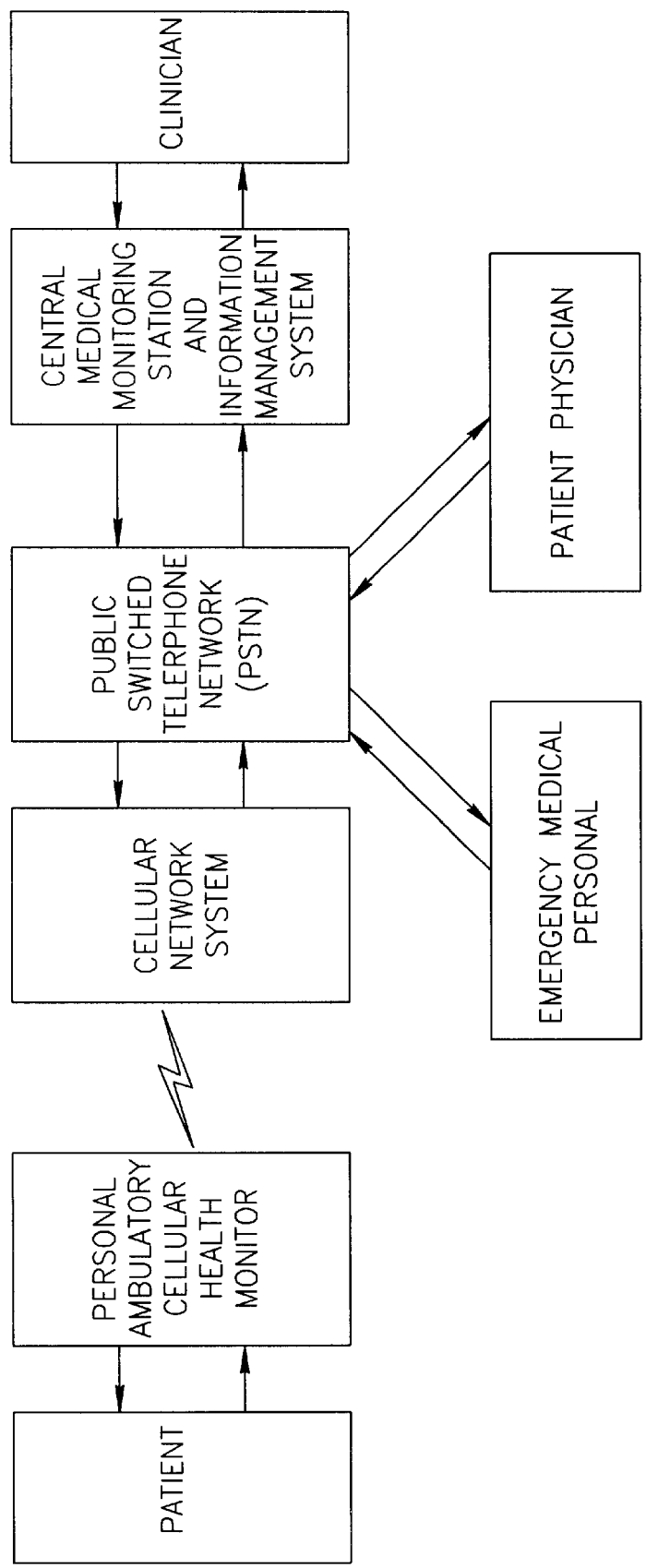
FIG. 4 is a simplified block diagram illustrating end-to-end communications between monitor 12 and a central medical monitoring station, constructed and operative in accordance with a preferred embodiment of the present invention.

Reference is now made to FIG. 4 which is a simplified block diagram illustrating end-to-end communication between monitor 12 and a central medical monitoring station 20, constructed and operative in accordance with a preferred embodiment of the present invention. Monitor 12 typically communicates with central medical monitoring station 20 via a cellular telephone network system 22 and a public switched telephone network (PSTN) 24. Central station 20 typically comprises conventional communications and data processing means for supporting voice and data communications with monitor 12 and patient 10. Patient 10 may communicate by voice channel via monitor 12 with a clinician 26 who is located at the central station 20. Monitor 12 may send and/or receive data to and/or central station 20 via a data communications channel. The clinician 26 may contact emergency medical personnel 28 and give them the patient's condition and location. The clinician 26 may also alert the patient'physician 30.

Monitor 12 typically operates in any of the following modes:

1. Event recording activated by the patient, either at the patient's initiative, the clinician's initiative, or pursuant to an alarm, where the patient performs one or more tests and transmits the data to the central station. In this mode the central station may be contacted at the beginning of the event for data transmission during the event or at the conclusion of the testing;

2. Continuous monitoring where physiological data are captured continuously and stored in memory for later transmission. Continuous monitoring may be provided in any of the following ways:

Patient-activated event recorder where pre-event/event/post-event data are transmitted to the central station;

Device-activated event recorder where physiological data are detected which fall outside preset parameters;

Holter-mode where data are transmitted automatically when memory becomes full, allowing memory to be cleared and monitoring to continue uninterrupted; and Holter-mode where data are transmitted by patient at any time, allowing memory to be cleared.

Figure 5:
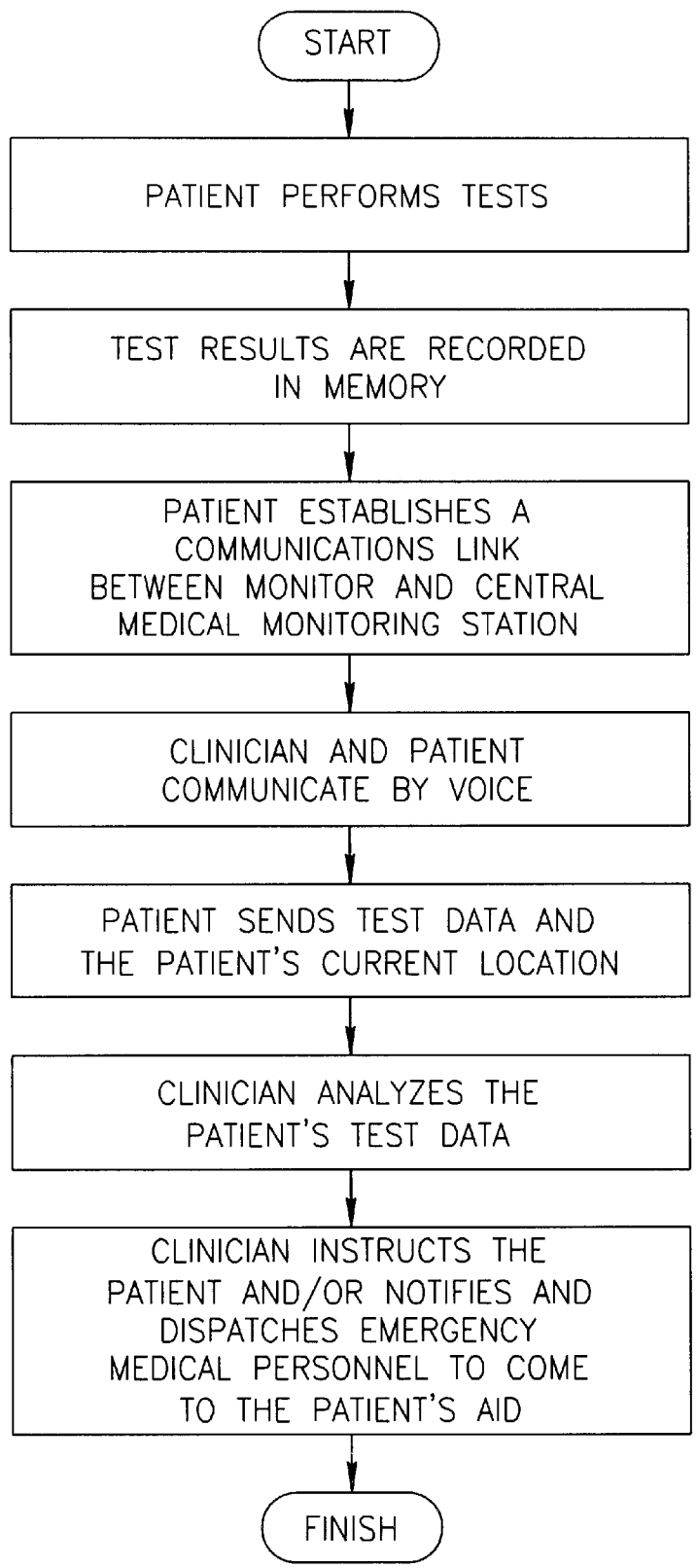
FIG. 5 is a simplified flowchart illustration of the operation of monitor 12 in event recording mode activated by patient, operative in accordance with a preferred embodiment of the present invention.

Reference is now made to FIG. 5 which is a simplified flowchart illustration of the operation of monitor 12 in event recording mode activated by patient, operative in accordance with a preferred embodiment of the present invention. In this mode monitor 12 is used by the patient to perform one or more types of physiological testing described hereinabove. The result of the tests are recorded in RAM memory 602 (FIG. 2). The patient then establishes a communications link between monitor 12 and a central medical monitoring station by dialing via keypad 607 and placing a cellular telephone call which is then connected to the public telephone network. When a clinician at the receiving station answers the call the clinician and patient may communications by voice. The patient may also send the stored data of the test results, as well as the patient's current location as determined by PLC subsystem 200. The clinician at the receiving station may analyze the patient's physiological data and may instruct the patient regarding any actions the patient should take and/or may notify emergency medical personnel of the patient's present location and dispatch them to come to the patient's aid.

Figure 6:
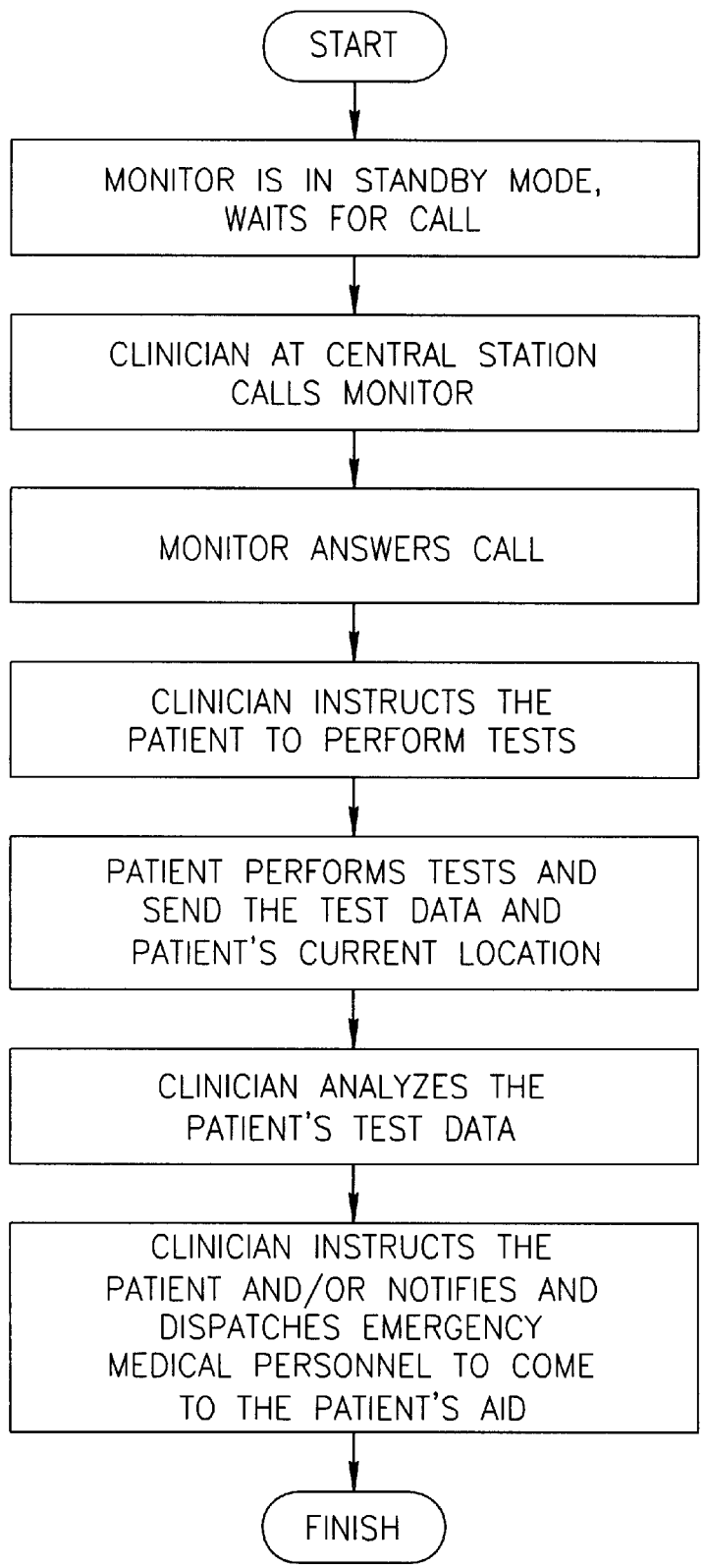
FIG. 6 is a simplified flowchart illustration of the operation of monitor 12 in event recording mode activated remotely by an operator at a central medical monitoring station, operative in accordance with a preferred embodiment of the present invention.

Reference is now made to FIG. 6 which is a simplified flowchart illustration of the operation of monitor 12 in event recording mode activated remotely by an operator at a central medical monitoring station, operative in accordance with a preferred embodiment of the present invention. In this mode monitor 12 is in a standby mode in which it is able to receive and automatically answer a call from a central medical monitoring station via cellular network. A clinician at central station connects to monitor 12 and, during a voice communication session with the patient, instructs the patient to perform one or more tests. The patient performs the tests and sends the test data, in addition to the patient's current location, to the central station. As above, the clinician at the receiving station may analyze the patient's physiological data and may instruct the patient regarding any actions the patient should take and/or may notify emergency medical personnel of the patient's present location and dispatch them to come to the patient's aid.

Figure 7:
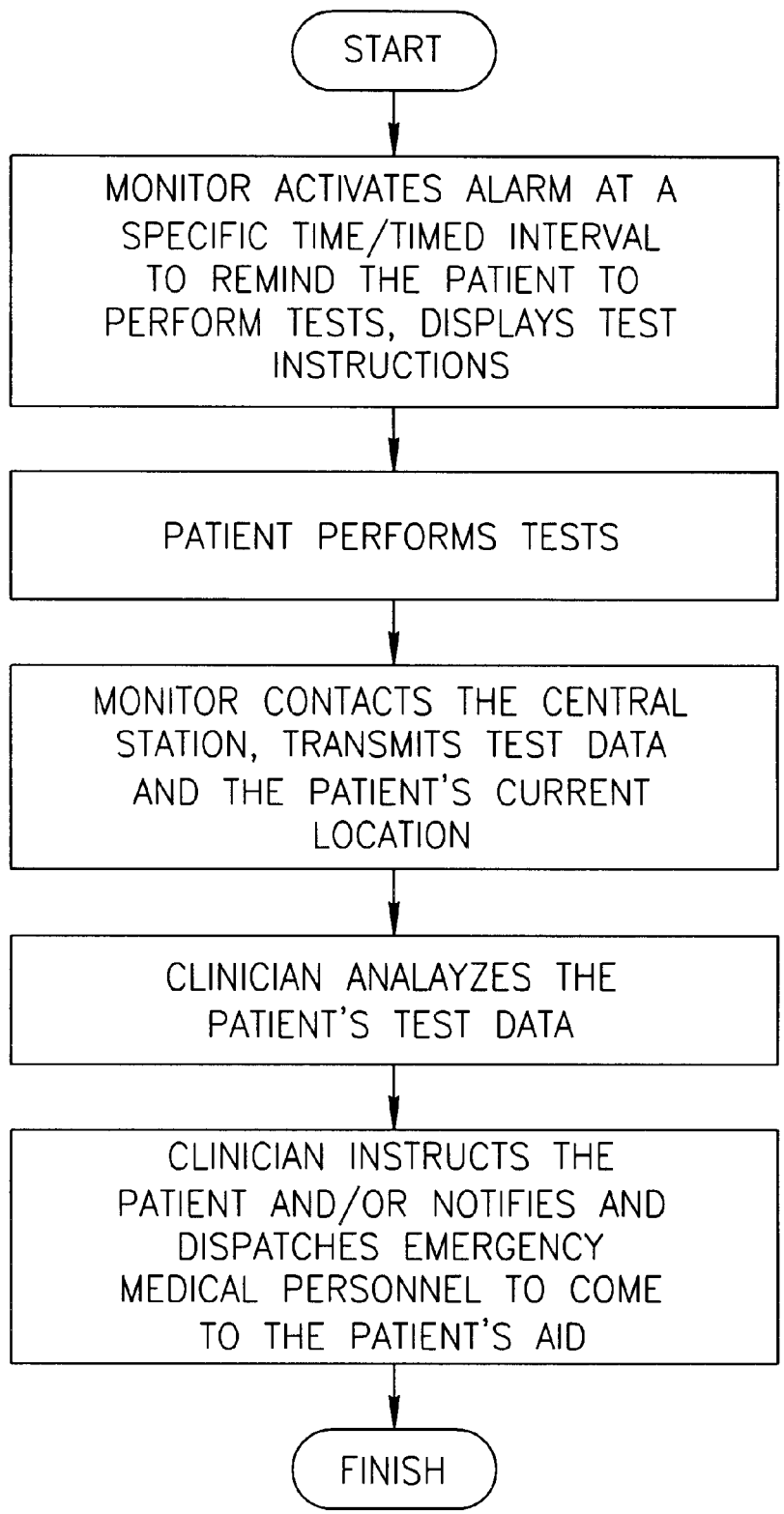
FIG. 7 is a simplified flowchart illustration of the operation of monitor 12 in event recording mode activated by the patient pursuant to an alarm, operative in accordance with a preferred embodiment of the present invention.

Reference is now made to FIG. 7 which is a simplified flowchart illustration of the operation of monitor 12 in event recording mode activated by the patient pursuant to an alarm, operative in accordance with a preferred embodiment of the present invention. In this mode monitor 12 is preprogrammed to activate alarm 609 (FIG. 2) at a specific time or at a timed interval, calculated using microprocessor 604's internal clock, in order to periodically remind the patient to perform one or more tests. Which tests to perform, as well as instructions for performing the tests, may appear on display 606 or may be heard via speaker 406 in accordance with preprogrammed instructions. The patient then performs the tests according to the instructions. Once the tests are completed, or at preset times or elapsed intervals, monitor 12 contacts the central station as described above and transmits the recorded physiological data and the patient's current location.

Figure 8:
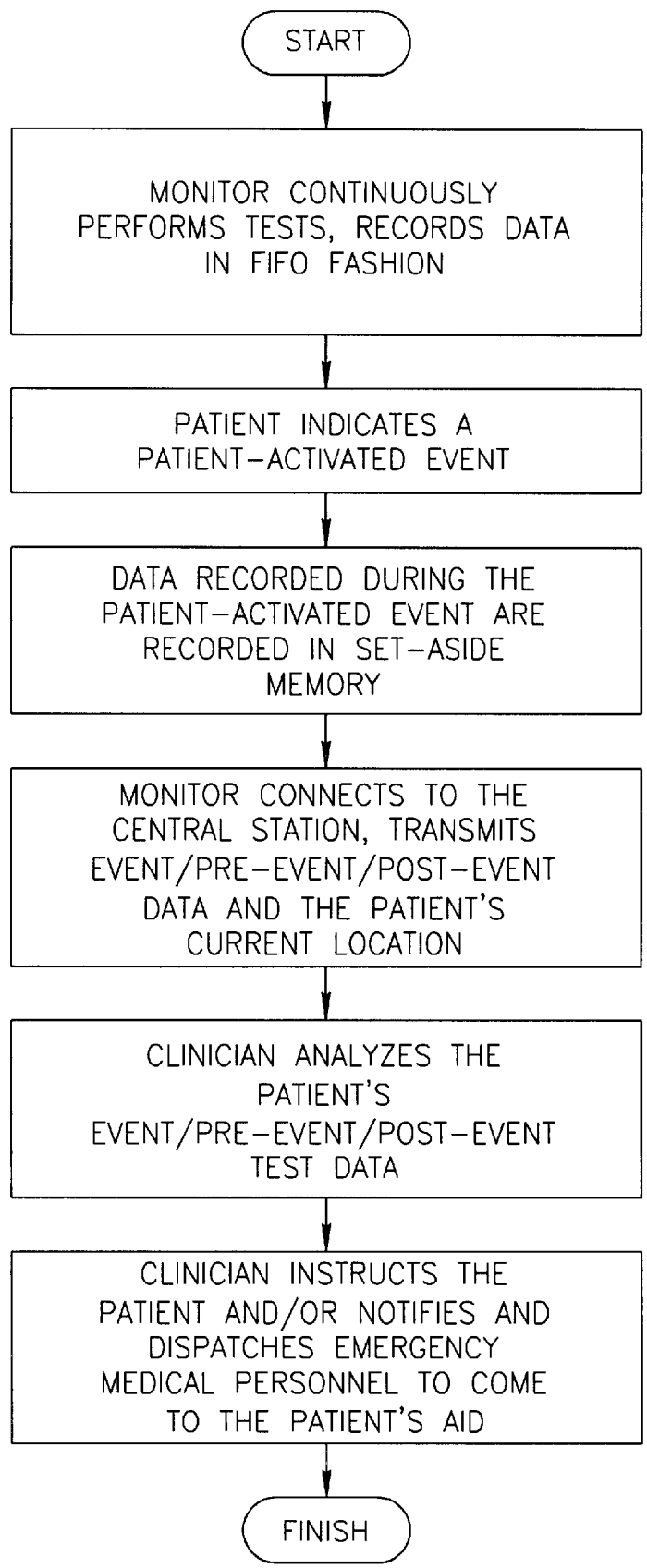
FIG. 8 is a simplified flowchart illustration of the operation of monitor 12 in combination continuous recording mode and patient-activated event recording mode, operative in accordance with a preferred embodiment of the present invention.

Reference is now made to FIG. 8 which is a simplified flowchart illustration of the operation of monitor 12 in combination continuous recording mode and patient-activated event recording mode, operative in accordance with a preferred embodiment of the present invention. In this mode monitor 12 continuously performs one or more tests and records the test data in RAM memory 602. Since RAM memory 602 is limited, data are stored in FIFO fashion, such that one RAM 602 becomes full, additional data are written over the oldest recorded data. The patient, sensing discomfort presses a button on keypad 607 to indicate a patient-activated event. The data recorded during the patient-activated event are recorded in an area of RAM memory that is set aside such that it is write-protected with respect to data recorded prior to and subsequent to the event and will not be overwritten once the event concludes, either after a predetermined elapsed time, after the patient signals the conclusion of the event, or upon receiving a signal from the central station. Once the patient initiates the patient-activated event monitor 12 automatically connects to the central station and transmits the data recording during the event. Monitor 12 may additionally transmit data recorded immediately prior to the event, such as the 60 seconds of data recorded prior to the event or any other preset length of time prior to the event, in addition to transmitting the patient's current location. Additionally or alternatively, any or all data recorded prior to the event and contained in RAM 602 may be transmitted to the central station. This will allow the clinician to compare pre-event data with event data, thus providing a comparison that may be more useful than event data alone. Monitor 12 may additionally transmit post-event data for a predetermined length of time or until the patient or the clinician instructs otherwise.

Figure 9:
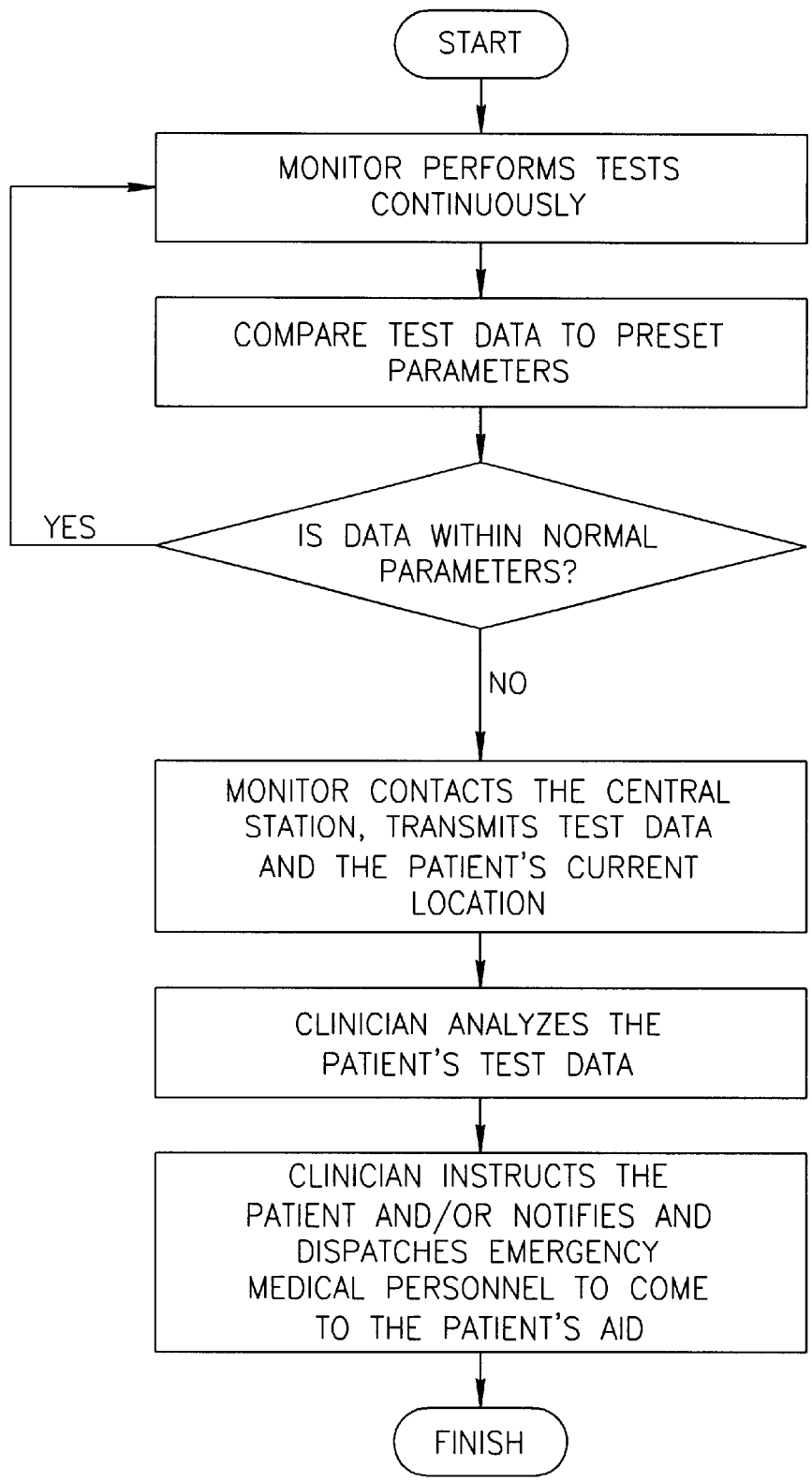
FIG. 9 is a simplified flowchart illustration of the operation of monitor 12 in continuous recording mode with a device-activated event recorder, operative in accordance with a preferred embodiment of the present invention.

Reference is now made to FIG. 9 which is a simplified flowchart illustration of the operation of monitor 12 in continuous recording mode with a device-activated event recorder, operative in accordance with a preferred embodiment of the present invention. In this mode monitor 12 performs one or more tests continuously. The patient's physiological condition is continuously monitored and the data are compared to preset parameters and recorded. If the data is falls outside the preset parameters monitor 12 automatically contacts the central station as above and send the recorded data as well as the patient's current location, allowing the clinician to analyze the data and take measures.

Figure 10:
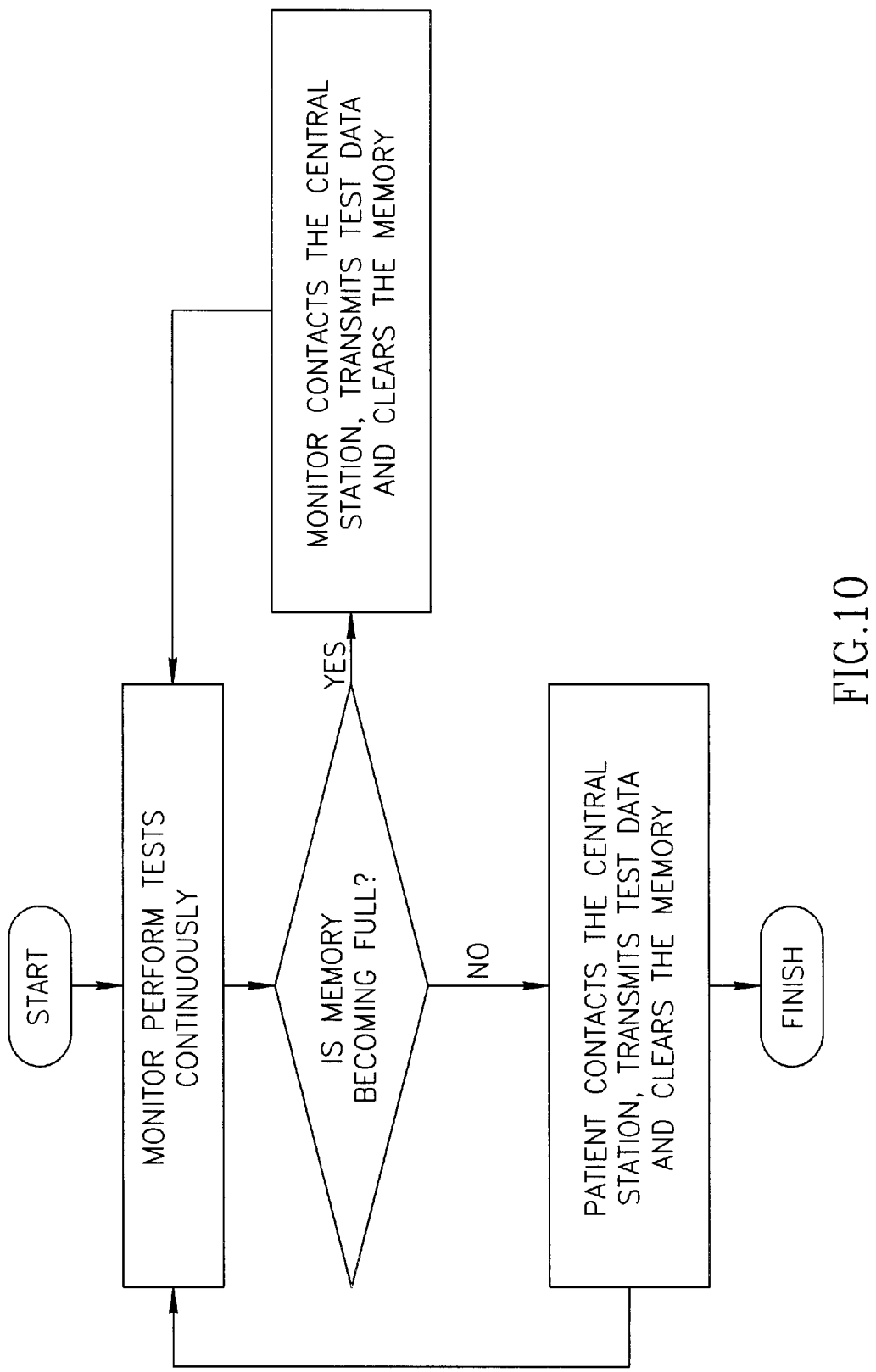
FIG. 10 is a simplified flowchart illustration of the operation of monitor 12 in continuous recording holter-mode with a device-activated or patient-activated data upload, operative in accordance with a preferred embodiment of the present invention.

Reference is now made to FIG. 10 which is a simplified flowchart illustration of the operation of monitor 12 in continuous recording holter-mode with a device-activated or patient-activated data upload, operative in accordance with a preferred embodiment of the present invention. In this mode monitor 12 performs one or more tests continuously. The patient's physiological data are continuously recorded. If memory becomes full monitor 12 automatically contacts the central station and uploads the data in memory, allowing memory to be cleared and monitoring to continue uninterrupted. Additionally or alternatively, the patient may initiate contact and data upload at any time, thus allowing memory to be cleared.

It is appreciated that in any of the above embodiments a clinician may remotely change present parameters stored in monitor 12 and may access a patient's recorded physiological data without patient intervention. It is also appreciated that any preprogrammed, predetermined, and preset instructions, information, parameters, and criteria described hereinabove with reference to monitor 12 may be stored in ROM memory 603 and/or RAM memory 602, as is well known in th art.

It is appreciated that various features of the invention which are, for clarity, described in the context of separate embodiments may also be provided in combination in a single embodiment. Conversely, various features of the invention which are, for brevity, described in the context of a single embodiment may also be provided separately on in any suitable combination.

It will be appreciated by persons skilled in the art that the present invention is not limited to what has been particularly shown and described hereinabove. Rather, the scope of the present invention is defined only by the that follow:

I claim:

1. Ambulatory patient monitoring apparatus comprising:
   a portable housing comprising:
   at least one physiological data input device operative to gather physiological data of said patient;
   location determination circuitry operative to determine geographic location information of said patient;
   cellular telephone communications circuitry for communicating said physiological data and said geographic location information to a central health monitoring station;
   voice communications circuitry whereby said patient conducts voice communications with a clinician at said central health monitoring station;
   digital signal processing circuitry for processing signals associated with any of said physiological data input device, said location determination circuitry, said cellular telephone communications circuitry, and said voice communications circuitry; and
   control circuitry for controlling any of said digital signal processing circuitry, said physiological data input device, said location determination circuitry, said cellular telephone communications circuitry, and said voice communications circuitry, wherein said control circuit comprises a memory for storing any of said physiological data and wherein said control circuitry is operative to simultaneously store a first portion of said physiological data in said memory in FIFO fashion and a second portion of said physiological data in said memory that is write-protected with respect to said first portion.

2. Apparatus according to claim 1 wherein said at least one physiological data input device is assembled within said housing.

3. Apparatus according to claim 1 wherein said at least one physiological data input device is at least partially external to said housing.

4. Apparatus according to claim 3 wherein said external portion of said at least one physiological data input device is connected to said via housing via a connector.

5. Apparatus according to claim 1 wherein said location determination circuitry comprises GPS circuitry.

6. Apparatus according to claim 1 wherein said control circuitry operates said physiological data input device continuously.

7. Apparatus according to claim 1 wherein said control circuitry operates said physiological data input device upon initiation by said patient.

8. Apparatus according to claim 1 wherein said memory comprises preset parameters adapted for comparison with said physiological data.

9. Apparatus according to claim 8 wherein said control circuitry is operative to determine whether said physiological data are within preset parameters.

10. Apparatus according to claim 9 wherein said control circuitry is operative to initiative contact with said central health monitoring station when said physiological data are determined to be outside of said preset parameters.

11. Apparatus according to claim 1 wherein said memory comprises preprogrammed instructions for output to said patient via either of a display and a speaker.

12. A system for monitoring a patient, the system comprising:
   a central health monitoring station; and
   a portable housing for use by said patient, the portable housing comprising:
      at least one physiological data input device operative to gather physiological data of said patient;
      location determination circuitry operative to determine geographic location information of said patient;
      cellular telephone communications circuitry for communicating said physiological data and said geographic location information to said central health monitoring station;
      voice communications circuitry whereby said patient conducts voice communications with a clinician at said central health monitoring station;
      digital signal processing circuitry for processing signals associated with any of said physiological data input device, said location determination circuitry, said cellular telephone communications circuitry, and said voice communications circuitry; and
      control circuit for controlling any of said digital signal processing circuitry, said physiological data input device, said location determination circuitry, said cellular telephone communications circuitry, and said voice communications circuitry wherein said control circuitry comprises a memory for storing any of said physiological data and wherein said control circuitry is operative to simultaneously store a first portion of said physiological data in said memory in FIFO fashion and a second portion of said physiological data in said memory that is write-protected with respect to said first portion.

13. A method for monitoring a patient, the method comprising:
   providing a portable housing for use by said patient, the portable housing comprising:
      at least one physiological data input device operative to gather physiological data of said patient;
      location determination circuitry operative to determine geographic location information of said patient;
      cellular telephone communications circuitry for communicating said physiological data and said geographic location information to said central health monitoring station;
      voice communications circuitry whereby said patient conducts voice communications with a clinician at said central health monitoring station;
      digital signal processing circuitry for processing signals associated with any of said physiological data input device, said location determination circuitry, said cellular telephone communications circuitry, and said voice communications circuitry; and
      control circuitry for controlling any of said digital signal processing circuitry, said physiological data input device, said location determination circuitry, said cellular telephone communications circuitry, and said voice communications; and
   gathering physiological data of said patient; and
   storing said physiological data in a memory wherein storing said physiological data comprises simultaneously storing a first portion of said physiological data in said memory in FIFO fashion and a second portion of said physiological data in said memory that is write-protected with respect to said first portion;
   determining the geographic location of said patient; and
   communicating said physiological data and said geographic location to said central health monitoring station.

14. A method according to claim 13 and further comprising:
   analyzing said physiological data; and
   providing a response based on said physiological data.

15. A method according to claim 13 wherein said gathering step is performed in response to activation by said patient.

16. A method according to claim 13 and further comprising activating an alarm prior to said activation by said patient.

17. A method according to claim 13 wherein said gathering step is performed independently from activation by said patient.

18. A method according to claim 13 wherein said communicating step is performed in response to activation by said patient.

19. A method according to claim 13 wherein communicating said physiological data and said geographic location is performed independently from activation by said patient upon said memory becoming full.

20. A method according to claim 19 and further comprising clearing a portion of said memory corresponding to said physiological data that has been communicated to said central health monitoring station.

21. A method according to claim 20 wherein said storing step comprises simultaneously storing a first portion of said physiological data in said memory in FIFO fashion and a second portion of said physiological data in said memory that is write-protected with respect to said first portion.

22. A method according to claim 13 wherein said communicating step comprises establishing a communications link with said central health monitoring station in response to activation by said patient.

23. A method according to claim 13 wherein said communicating step comprises established a communication link with said central health monitoring station in response to an incoming communication from said central health monitoring station.

24. A method according to claim 13 wherein said communicating step comprises:

determining whether said physiological data are outside of preset parameters; and establishing a communications link with said central health monitoring station when said physiological data are determined to be outside of said preset parameters.

25. A method according to claim 14 wherein said providing a response step comprises voice-communication an instruction to said patient.

26. A method according to claim 14 wherein said providing a response step comprises providing said patient's location to medical emergency personnel and dispatching said personnel to said patient's location.

* * * * *